(12) United States Patent
Huang

(10) Patent No.: US 11,844,852 B2
(45) Date of Patent: Dec. 19, 2023

(54) SKINCARE PRODUCT AND METHOD OF PREPARATION THEREOF

(71) Applicant: FE:I BEAUTY TECH, INC., Wilmington, DE (US)

(72) Inventor: Xi Huang, Montvale, NJ (US)

(73) Assignee: FE:I BEAUTY TECH, INC., Wilmington, DE (US)

( * ) Notice: Subject to any disclaimer, the term of this patent is extended or adjusted under 35 U.S.C. 154(b) by 109 days.

(21) Appl. No.: 17/062,065

(22) Filed: Oct. 2, 2020

(65) Prior Publication Data

US 2021/0015725 A1 Jan. 21, 2021

Related U.S. Application Data

(63) Continuation-in-part of application No. 14/380,679, filed as application No. PCT/IB2013/051438 on Feb. 22, 2013, now Pat. No. 10,792,240.

(30) Foreign Application Priority Data

Feb. 23, 2012 (CN) .......................... 201210041549.6

(51) Int. Cl.
*A61K 8/24* (2006.01)
*A61K 8/25* (2006.01)
*A61K 8/67* (2006.01)
*A61Q 19/08* (2006.01)

(52) U.S. Cl.
CPC .................. *A61K 8/24* (2013.01); *A61K 8/25* (2013.01); *A61K 8/671* (2013.01); *A61K 8/676* (2013.01); *A61K 8/678* (2013.01); *A61Q 19/08* (2013.01); *A61K 2800/60* (2013.01)

(58) Field of Classification Search
None
See application file for complete search history.

(56) References Cited

U.S. PATENT DOCUMENTS 10,792,240 B2 * 10/2020 Huang ..................... A61K 8/19
2010/0086606 A1 * 4/2010 Ogawa ................. A61K 9/1611
977/773

FOREIGN PATENT DOCUMENTS

WO WO-9956720 A1 * 11/1999 ............... A61K 8/19

OTHER PUBLICATIONS

Wikipedia—Vitamin C, accessed at https://en.wikipedia.org/wikiVitamin_C on Sep. 9, 2017. (Year: 2017).*

(Continued)

*Primary Examiner* — Dominic Lazaro
(74) *Attorney, Agent, or Firm* — Gearhart Law, LLC

(57) ABSTRACT

The core active components of the present composition, termed as de-ironizing inducers (DII), has a reducing agent and a precipitating agent. Molar ratios of the reducing agent with the precipitating agent range from 1:3-6 and the core components in the skincare product range from 0.1% to 10% w/w. The pH value of the skincare product is between 6.6 and 7.4. The skin care products can safely and effectively 5 remove iron in the skin, which has been shown to accelerate the visible signs of aging. The core components can also be used in combination with conventional skincare product compounds to achieve better anti-aging effects.

15 Claims, 7 Drawing Sheets

(56) References Cited

OTHER PUBLICATIONS

Wikipedia—Calcium Carbonate, accessed at https://en.wikipedia.org/wiki/Calcium_carbonate on Sep. 9, 2017 (Year: 2017).*
Y. Zou, et al., Associations of serum retinal, alpha-tocopherol, and gammatocopherol with biomarkers among healthy Japanese men, Int. J. Environ. Res. Public Health, 11 (2014) 1647-60. (Year: 2014).*
Link, G., et al., Iron loading modifies the fatty acid composition of cultured rat myocardial cells and liposomal vesicles: effect of ascorbate and alpha-tocopherol on myocardial lipid peroxidation, J. Lab. Clin. Med., 114 (1989) pp. 243-249. (Year: 1989).*
M.E. Aliaga, et al., Superoxide-dependent reduction of free Fe(3+) and release of Fe(2+) from ferritin by the physiologically-occurring Cu(l)-glutathione complex, Bioorg. Med. Chem. 19 (2011) pp. 534-541. (Year: 2011).*
M.B. Zimmermann, et al., Vitamin A supplementation in children with poor vitamin A and iron status increases erythropoietin and hemoglobin concentrations without changing total body iron, The Am. J. Clin. Nutr., 84 (2006) pp. 580-586 (Year: 2006).*
L.L. Munasinghe, et al., The Effect of Serum 25-Hydroxyvitamin D on Serum Ferritin Concentrations: A Longitudinal Study of Participants of a Preventive Health Program, Nutrients, 11 (2019). p. 692 (Year: 2019).*

* cited by examiner

Before use

After use

SKINCARE PRODUCT AND METHOD OF PREPARATION THEREOF

CLAIM OF PRIORITY

This application claims priority to U.S. application Ser. No. 14/380,679 filed on Aug. 22, 2014 which is a § 371 national stage entry of PCT/IB13/051438 filed on Feb. 22, 2013 which claims priority to Chinese Patent Application 201210041549.6 filed on Feb. 23, 2012, the entire contents of all of which are herein fully incorporated by reference in its entirety.

FIELD OF THE EMBODIMENTS

This application introduces a novel class of skincare products aimed at removing iron in the skin and its preparation method.

BACKGROUND OF THE EMBODIMENTS

Across a woman's lifespan of, menopause has the greatest impact on her health. Due to menopause, the structure and function of the skin is changed more than any other organs. During menopausal transition and after menopause, the skin becomes thinner, drier, and forms more wrinkles than before menopause. These ailments are mainly due to the decrease in collagen content and its ability to maintain humidity. Therefore, the skin becomes more susceptible to damage caused by environmental factors such as ultraviolet (UV) light and ozone (Miguel, J., Ramirez-Bosca, A., Ramirez-Bosca, J. V., and Alperi, J. D. 2006. Menopause: a review on the role of oxygen stress and favorable effects of dietary antioxidants. *Arch Gerontol Geriatr* 42:289-306). We have found that, after menopause, serum levels of ferritin, an iron storage protein with a capacity of binding up to 4,500 atoms of iron per molecule of ferritin and an indicator of body iron status, were increased 2 to 3-fold (FIG. 1) (Jian, J., Pelle, E., and Huang, X. 2009. Iron and menopause: does increased iron affect the health of postmenopausal women? *Antioxid Redox Signal* 11:2939-2943). Ferritin levels in the skin increase by 40% (FIG. 2). After conversion, we have found that serum ferritin concentration in women is between 0.94-1.3 ng/mg protein. The average concentration of ferritin in postmenopausal skin is about 542 ng/mg protein (FIG. 2). Thus, our study has shown that ferritin concentration in the skin is 400 to 575 times higher than that in serum. Because the human body has no other means to excrete iron, except menstruation and desquamation, skin becomes a very important target for iron in peri- and postmenopausal woman (Andrews, N.C. 1999. Disorders of iron metabolism. *N Engl J Med* 341:1986-1995).

Increased iron can produce large amounts of free radicals in the skin. In addition, we have also found that increased iron sensitizes skin to ultraviolet (UV) light, causing UVA-mediated damage (FIG. 3) (ban, J., Pelle, E., Yang, Q., Pernodet, N., Maes, D., and Huang, X. 2011. Iron sensitizes keratinocytes and fibroblasts to UVA-mediated matrix metalloproteinase-1 through TNF-alpha and ERK activation. *Exp Dermatol* 20:249-254). For example, after exposure to UVA, matrix metalloproteinase-1 (MMP-1) activity was significantly increased in primary human dermal fibroblast with a high iron concentration when compared to the same fibroblasts containing a normal iron concentration (Jian, J., Pelle, E., Yang, Q., Pernodet, N., Maes, D., and Huang, X. 2011. Iron sensitizes keratinocytes and fibroblasts to UVA-mediated matrix metalloproteinase-1 through TNF-alpha and ERK activation. *Exp Dermatol* 20:249-254). Until now, estrogen deficiency has been considered the main cause of skin aging in middle-aged women (Brincat, M. P., Baron, Y M., and Galea, R. 2005. Estrogens and the skin. *Climacteric* 8:110-123). However, according to our findings, a decrease in estrogen is not the sole cause of skin thinning, loss of skin elasticity, increase of wrinkle formation, and sensitization of skin to sun exposure in postmenopausal women. Because estrogen replacement therapy increases the risk of cancer (Nelson, H. D., Humphrey, L. L., Nygren, P., Teutsch, S. M., and Allan, J. D. 2002, Postmenopausal hormone replacement therapy: scientific review. *Jama* 288.872-881), it is necessary to develop other alternatives.

Iron is an essential element in the human body. It is an important component of heme, which is responsible for transporting oxygen in red blood cells. Iron is also involved in DNA synthesis and other enzymatic functions. Excess iron is stored in ferritin and excreted through skin desquamation. Ferritin is a major source of iron in the skin and sensitizes skin to sun exposure and oxidative damage. Thus, removal of iron from ferritin can improve skin appearance. At the present, iron chelation is the main therapy to remove iron from human body. However, iron chelators are chemicals, and they have considerable side effects. For example, chelating agents are mainly used for detoxification of metal poisoning or removal of excess iron due to blood transfusion. In the case of treating iron overload, they are usually administered by intravenous or intraperitoneal injection (Jomova, K., and Valko, M. 2011. Importance of Iron Chelation in Free Radical-Induced Oxidative Stress and Human Disease. *Curr Pharm Des* 17:3460-3473).

Currently, there is a novel class of iron chelators to prevent skin photoaging (Yiakouvaki, A., Savovic, J., Al-Qenaei, A., Dowden, J., and Pourzand, C. 2006. Caged-iron chelators a novel approach towards protecting skin cells against UVA-induced necrotic cell death. *J Invest Dermatol* 126:2287-2295). Under normal physiological conditions, this type of iron chelator has no ability to chelate iron. However, after exposure to UVA, it is activated and then chelates iron. This type of chelating agents is called "caged" iron chelator. Unfortunately, because they are chemicals, they may have different degrees of side effects on the skin.

Until now, the prior art has not specifically targeted iron in the skin. Therefore, from the clinical point of view, it is very important to search for better methods and products to remove iron in skin than chelating. The Chinese patent application CN1965801A disclosed skincare products, which were actually placed into two separate packages: Body Lotion and Revitalizing Factor. This patent application only considered the effective absorption of the ingredients and did not consider the effectual removal of iron. The body lotion is an emulsion with an acidic pH. The Revitalizing Factor is a powder with an alkaline pH. Because the acidic and alkaline properties of the two packages, they were not mixed together. In addition, this patent application used nanoparticles and nanoparticles might penetrate into the circulation system and cause toxicity.

SUMMARY OF THE EMBODIMENTS

Shortcomings of existing technologies in the current market of skincare products include: iron chelators' toxicity to the skin cells; lack of available skincare products that safely and effectively remove iron in the skin. Thus, current skincare products' anti-aging effects are limited. The present invention develops a novel class of skincare products that remove iron in the skin and provides a preparation method for them.

The technical solutions provided by the present invention are as follows:

The ingredients in the new skincare products include matrix and core components. The core components consist of a reducing agent(s) and a precipitating agent(s), wherein the molar ratio of the reducing agent to the precipitating agent is 1:3-6, preferably 1:5; core components in the skincare products represents 0.1%-10% w/w, preferably 5%; pH values of the skincare product is between 6.6 and 7.4, preferably 7; particle diameter of the skincare precipitating agent is in the submicron range (0.1-1 microns). In addition, the matrix is made of conventional skincare compounds;

Wherein the reducing agent is selected from vitamin C, vitamin E, glutathione, vitamin A, vitamin D, and their derivatives;

Wherein the precipitating agent is selected from pearl powder, calcium carbonate, calcium citrate, calcium phosphate, calcium silicate, calcium molybdate, calcium tungstate, magnesium carbonate, magnesium phosphate, magnesium silicate, magnesium selenate, barium carbonate, barium phosphate, barium silicate, barium oxalate, barium molybdate, barium manganate, barium selenate, beryllium carbonate, beryllium phosphate, beryllium silicate, strontium carbonate, strontium phosphate, strontium silicate, strontium molybdate, strontium tungstate, strontium selenate, and a combination thereof A method to prepare the novel class of iron-removing skincare products as stated in the present invention comprises the following steps:

1. Grind the particles of the precipitating agent to a particle size of 1-5 microns, preferably 1-3 microns;
2. Suspend the particles of the precipitating agent at a concentration of 100 mg/mL in deionized and nitrogen-saturated water and stir so that small particles float in the upper part and larger particles remain in the lower part of the container;
3. Slowly add the reducing agent into the bottom of the precipitating agent suspension. This is to use the acidity of the reducing agent to shrink the particle size of the precipitating agent into submicron particles (0.1 micron to 1 micron). After the reaction is complete without bubbles simmering, gently heat the reaction mixture to 45° C. Under vacuum conditions, reduce the volume of the reaction mixture by about 50%. Obtain the skincare core components with a final molar ratio of the reducing agent to the precipitating agent between 1:3-6, preferably 1:5;
4. Put the core components into the matrix. After mixing, the core components represent 0.1%-10% (w/w). Adjust the pH to 6.6-7.4.

Wherein the stirring speed in step (2) is 200-500 rotation per minute;

Wherein the molar ratio of the reducing agent to the precipitating agent and the relative concentration of the core components in the skincare products play important roles in the ability of the skincare products to remove iron. If the amount of the precipitating agent exceeds that of the reducing agent, it could favor the reaction toward iron precipitation immediately after its reduction. The core components need to reach certain concentrations in order to effectively eliminate iron in the skincare products;

Wherein the particle size of the precipitating agent is critical; in the sub-micron range, the precipitating agent can penetrate into the epidermis of the skin, but not into the blood circulation system.

In this invention, the reducing agent is preferably vitamin C, while the precipitating agent is preferably calcium carbonate.

Ferritin, one of the major proteins, sensitizes skin to sun exposure by strongly inducing matrix metalloproteinase (MMP-1) activity. Thus, the present invention is aimed to remove iron from ferritin. Ferritin has a strong binding affinity for trivalent (ferric) iron but no affinity for divalent (ferrous) iron. According to this physic-chemical characteristic, the present invention uses a reducing agent, such as vitamin C, to release iron from ferritin (FIG. 4). If only vitamin C is used, iron can be released from ferritin, but it can also continue to exert its harmful effect. To prevent this from occurring, the present invention employs a natural product calcium carbonate ($CaCO_3$) to precipitate the released iron (FIG. 5). Calcium carbonate is water insoluble and its neutral pH can easily cause iron precipitation immediately after its release from ferritin by vitamin C Of course, if only calcium carbonate is used, it cannot effectively precipitate iron, because iron is still stored in ferritin.

Compared with the prior art, the beneficial effects of the present invention are as follows:

1. A mixture of vitamin C and calcium carbonate can effectively decrease iron-mediated ferritin formation (FIG. 6) as well as inhibit lipid peroxidation (FIG. 7) in primary normal human epidermal keratinocytes;
2. The present invention uses a mixture of vitamin C and calcium carbonate as a de-ironizing inducer (DII) and adds this mixture to the skincare products so that it makes up to 0.1%-10% (w/w) of the product. The high concentration of the core components is capable of reducing iron and precipitating iron and, thus, effectively removes iron from ferritin. Through the simultaneous use of the two natural products in two steps with the first step to reduce iron from ferritin, followed by precipitation of iron in the skin, this invention achieves the goal of preventing aging in postmenopausal skin.
3. The preparation method proposed in the present invention can powerfully produce submicron (0.1 micron to 1 micron) particles of calcium carbonate (FIG. 8), while preserving the reducing ability of the vitamin C Vitamin C and calcium carbonate are pre-mixed to produce sub-micron particles (0.1 micron to 1 micron). These sub-micron particles (0.1 micron to 1 micron) can effectively enter into the skin (FIG. 9) and remove iron from the skin. Yet, they do not penetrate into the blood circulation system. The clinical trials showed that the mixture of the two can be the best in removing iron from the skin and preventing skin from aging (FIG. 10).
4. The skincare products in the present invention have a neutral pH, which stabilizes vitamin C and calcium in the products.

DETAILED DESCRIPTION OF EMBODIMENTS

In conjunction with the drawings and the embodiments, the present invention is further explained in detail as below:

Embodiment 1

Figure 1:
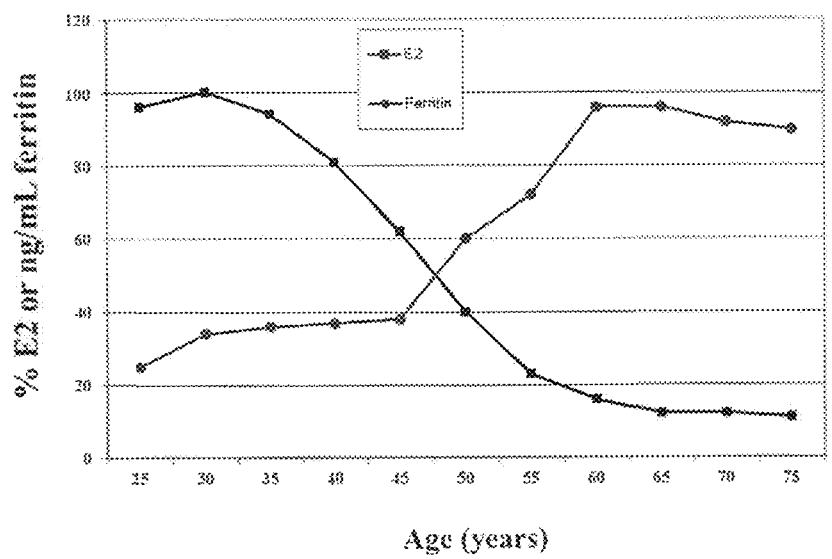
FIG. 1. Concurrent but inverse changes of ferritin versus estrogen during menopausal transition.

Changes in estrogen and ferritin levels during menopausal transition: Serum levels of 17β-estradiol (E2) were converted to % of peak value at 500 µg/mL serum at age 25. Levels of ferritin were expressed as ng/mL serum. E2 data as a function of age were obtained from website http://www.drlam.com/A3R_brief_in_doc_format/Estrogen Dominance cfm. Ferritin data were obtained from the Third National Health and Nutrition Examination Survey (NHANES III) in the United States (FIG. 1).

Figure 2:
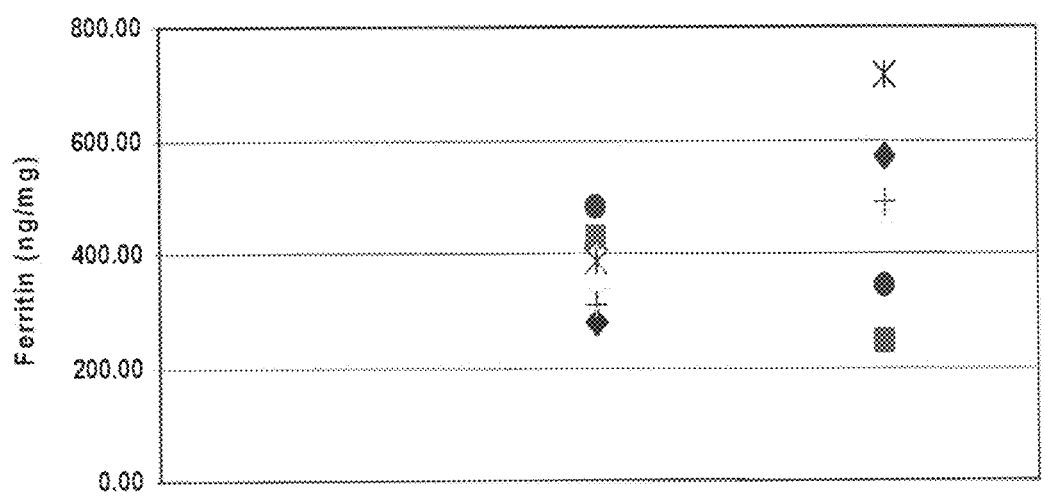
FIG. 2. Differences in levels of ferritin between skin biopsy samples of pre- and post-menopausal women.

Human studies: Studies were performed after informed consent was obtained according to an approval from the local Institutional Review Board. Human skin 3 mm punch biopsy samples were obtained from six pre- and six post-menopausal women by punching the upper, inner left and right arms. Skin weights ranged from 3 to 50 mg. After grinding with a Dremel mini-Tissue Homogenizer in 400 µl M-PER lysis buffer in the presence of a protein inhibitor cocktail (Pierce Biotechnology Inc., Rockford, Ill.), protein extracts were collected after removing debris by centrifugation. The concentrations of total protein extracted from the skin samples were determined by bicinchoninic acid (BCA) assay. The remaining protein extracts were used for measurements of ferritin. Two data points (left and right arm) per subject were presented in the study. Results were expressed as ng ferritin per mg of total protein and are presented in FIG. 2. Mean age of post-menopausal women was 58.8±1.3 year old (n=5) and mean level of ferritin in the post-menopausal skin was 542.4 ng/mg protein. Mean age of pre-menopausal women was 41.6±1.7 year old (n=6) and mean level of ferritin in pre-menopausal skin was 381.6 ng/mg protein. It is noteworthy that one outlier from post-menopausal skin with a left arm ferritin of 2,360.2 ng/mg protein and a right arm ferritin of 989.0 ng/mg protein was excluded in the analyses. Otherwise, the difference would be even more significant (FIG. 2).

Figure 3:
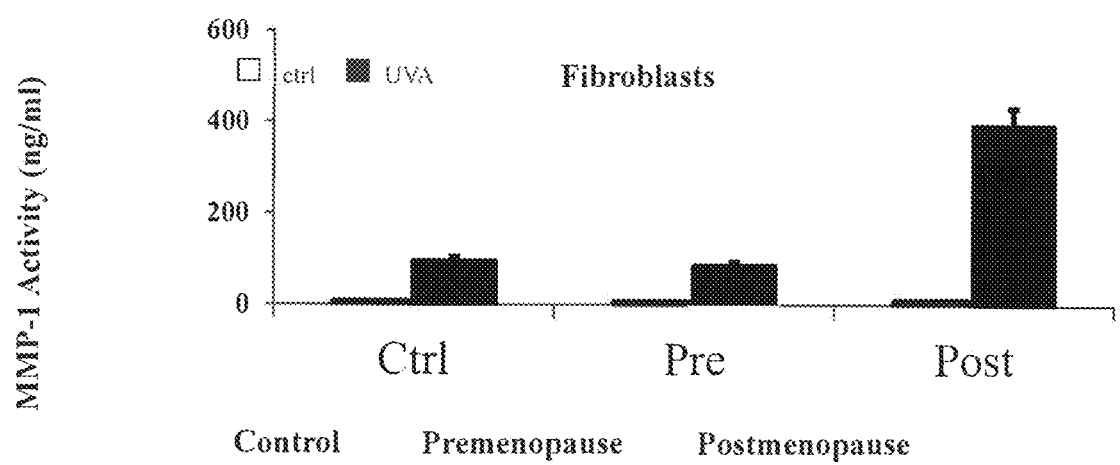
FIG. 3. Effects of UVA and iron on MMP-1 activities in primary human dermal fibroblasts.

Cell culture and UVA exposure: Primary human dermal fibroblasts were seeded in 6-well plates and starved in 0.1% fetal bovine serum (FBS)-containing Dulbecco's Modified Eagle Medium (DMEM). According to FIG. 1, two cell culture conditions were developed with the low estrogen and high iron mimicking postmenopausal women and high estrogen and low iron simulating premenopausal women. In premenopausal condition (Pre-), level of 17β-estradiol (E2) in the cell culture media is 500 ng/ml and that of apo-transferrin (Tf, without iron) is 5 µg/ml. In postmenopausal condition (Post-), level of ferritin is 20 ng/ml and that of holo-Tf (iron is 100% saturated in the two binding sites of TO is 5 µg/ml. After overnight starving, fibroblasts grown under either the control, Pre-, or Post-conditions were exposed to UVA at 50 kJ/m². Media were collected 24 h later for measurements of matrix metalloproteinase-1 (MMP-1) activities. MMP-1 activities were measured by Förster resonance energy transfer (FRET) assay following the Manufacturer's protocol (AnaSpec, San Jose, Calif.). Briefly, 100 µl sample or 100 µl standard were added in the plate pre-coated with anti-MMP-1 antibody for 2 h. After washing, MMP fluorogenic substrate, 5-FAM/QXL™ 520 FRET peptide, were added and cultured for 16 h at room temperature. The fluorescence is measured at Ex/Em=490 nm/520 nm upon MMP-1-induced cleavage of the FRET substrate. Results show that there were no differences in background levels of MMP-1 in fibroblasts grown under Pre or Post-menopausal conditions. However, UVA significantly induced MMP-1 activities in primary human dermal fibroblasts grown under Post-condition as compared to fibroblasts grown under the control or Pre-conditions (FIG. 3).

Figure 4:
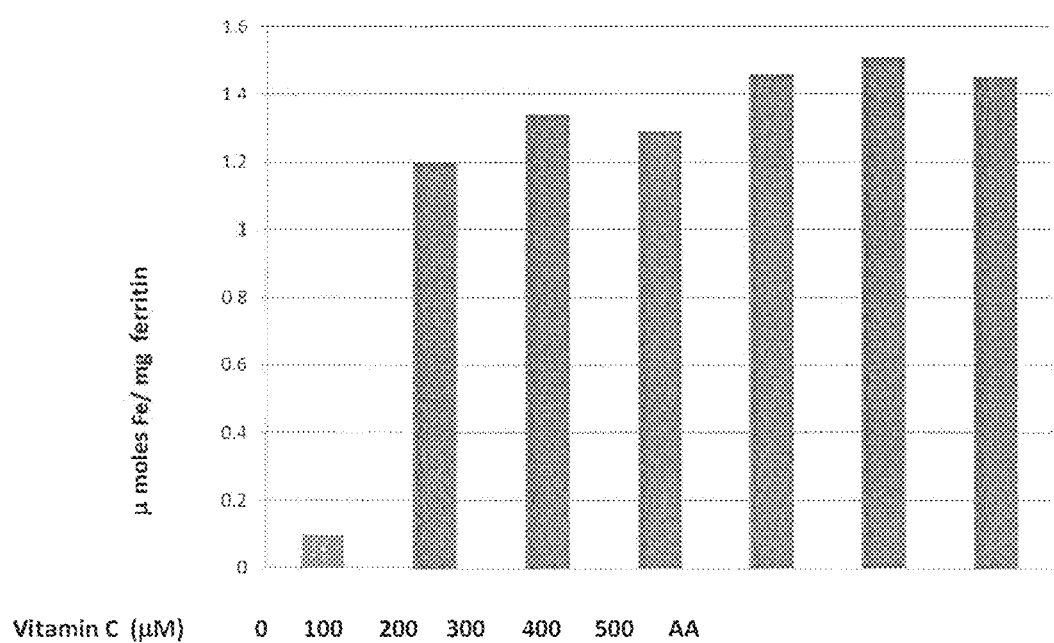
FIG. 4. Reducing effects of vitamin C on iron from ferritin.

Reduction of iron from ferritin by vitamin C. Ferritin at a concentration of 1 mg/ml was incubated with various concentrations of vitamin C (0-500 µM). After one hour incubation, the solutions were filtered using a membrane with a molecular weight cutoff of 5,000 Dalton (Millipore). Levels of iron in the filtrates were measured by Ferrozine (Sigma, St. Louis, Mo.), which forms a stable magenta-colored complex ($Fe^{2+}$-ferrozine) with a maximum absorption at 560 nm. In brief, 30 µl sample was added to 135 µl buffer. After 10 min incubation at 37° C., the absorbance was measured at 560 nm using a UV—visible microplate reader (SpectraMax Plus, Molecular Devices, Sunnyvale, Calif.). Then, 5 µl iron chromogenic agent (ferrozine) was added and after 15 min incubation, the absorbance was measured again at 560 nm. The difference in absorbance was used to calculate iron concentration after comparing to the iron standard curve. To determine whether iron is completely released from ferritin, atomic absorption (AA) was used to measure total iron in ferritin. Results show that high concentration of vitamin C is effective in releasing iron from ferritin. Atomic absorption (AA) confirmed that all iron in ferritin is released after vitamin C reduction (FIG. 4).

Figure 5:
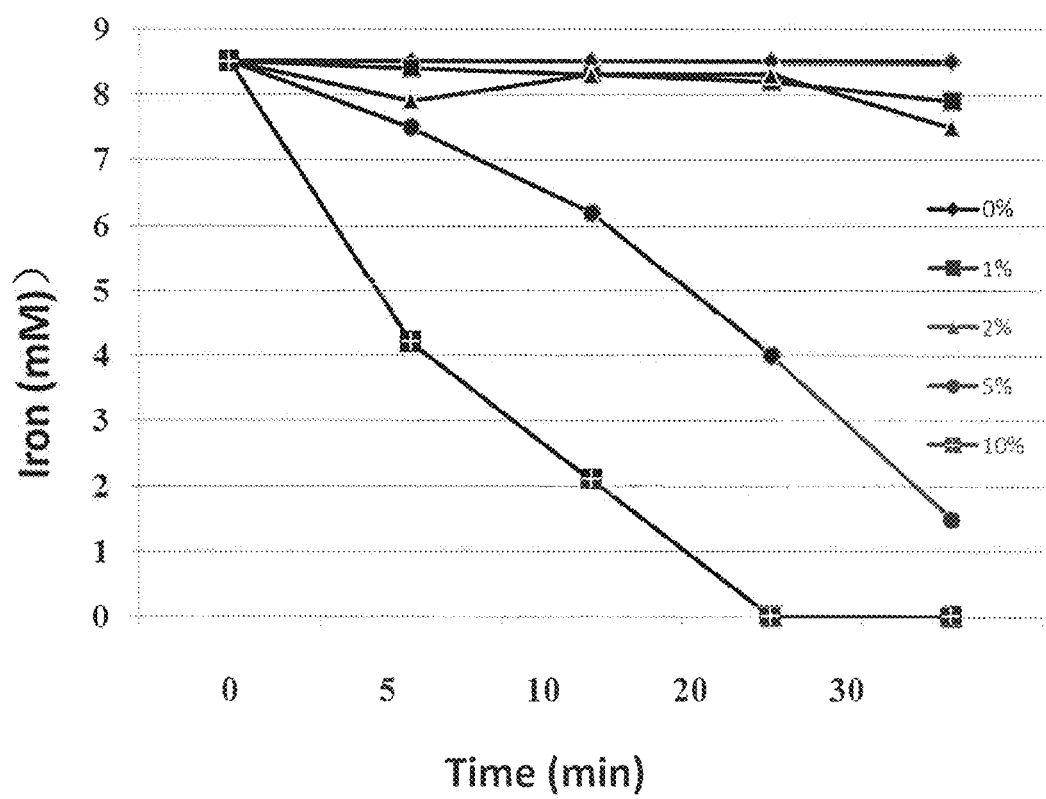
FIG. 5. Precipitating effects of calcium carbonate on iron.

Precipitation of iron by calcium carbonate: Iron was added to extracellular matrix, followed by the addition of different concentrations of calcium carbonate (0-10%) (FIG. 5). After various time periods of incubation, a small part of the mixture was filtered using a membrane with a molecular weight cutoff of 5,000 Dalton as previously described in FIG. 4. Levels of iron in the filtrates were determined by Ferrozine. Results show that calcium carbonate can effectively precipitate iron in the cellular matrix.

Figure 6:
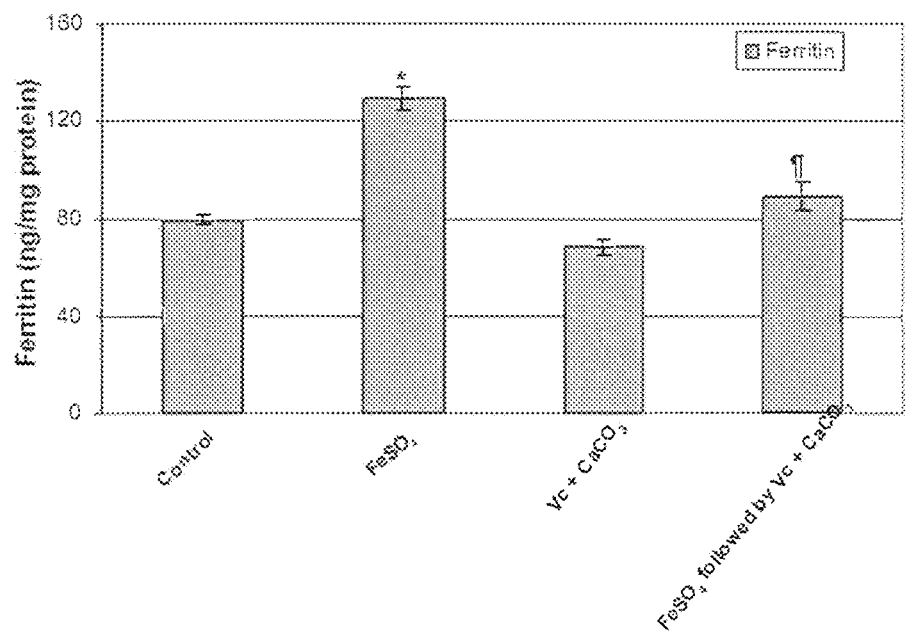
FIG. 6. Inhibition of ferritin formation by the core components of the invention.

Inhibition of ferritin formation by the core components: Primary normal human epidermal keratinocytes (NHEK) were seeded in 6-well plates. The cells were pretreated with 50 µM ferrous sulfate for 4 h, followed by a mixture of vitamin C and calcium carbonate at 10 µg/cm² for 20 h. After washing, the cells were collected and the proteins were extracted in lysis buffer. After determining protein concentration, a small portion of the protein was used for the measurement of ferritin. Results show that a mixture of vitamin C and calcium carbonate can effectively decrease ferrous sulfate-induced ferritin formation in NHEK (FIG. 6).

Figure 7:
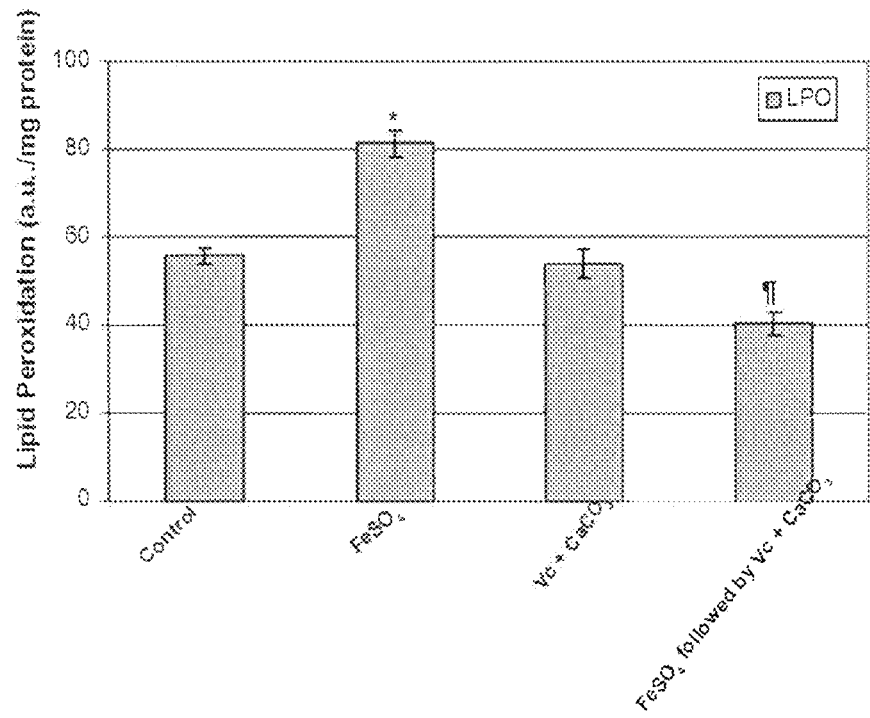
FIG. 7. Inhibition of lipid peroxidation by the core components of the invention.
Figure 8:
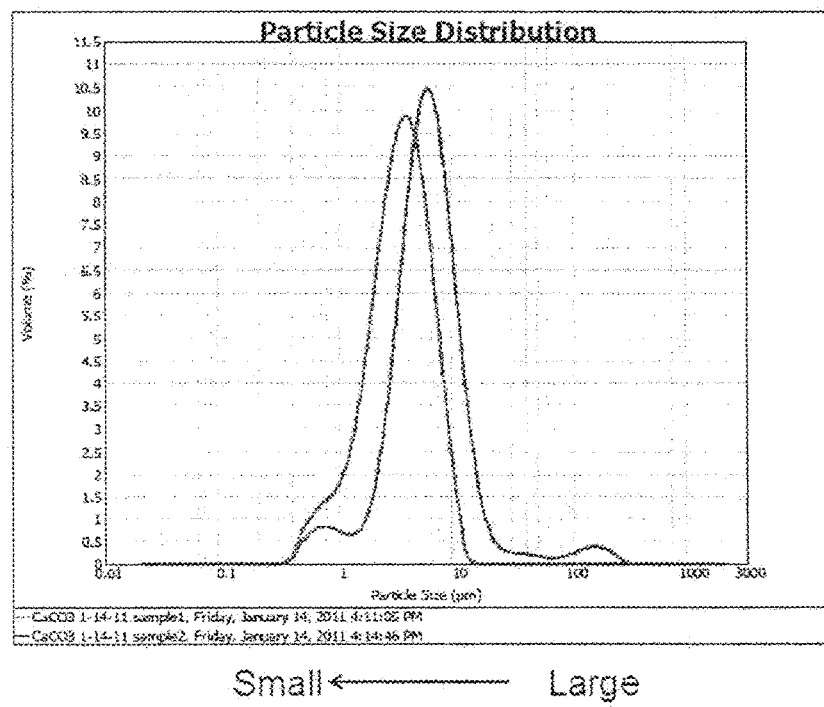
FIG. 8. Analyses of particle size of calcium carbonate with or without vitamin C treatment.

Inhibition of lipid peroxidation by the core components: NHEK cells were treated as described in FIG. 6. After centrifugation, cell debris was collected for measurements of lipid peroxidation using thiobarbituric acid assay. Results show that a mixture of vitamin C and calcium carbonate can effectively inhibit ferrous sulfate-induced lipid peroxidation in primary NHEK cells (FIG. 7).

Embodiment 2

Suspend calcium carbonate with particles size of approximate 2 μm at 100 mg per ml in deionized and nitrogen-saturated water.

1. Grind calcium carbonate to a particle size of approximately 2 μm; (2) Suspend calcium carbonate at 100 mg per ml in deionized and nitrogen-saturated water in order to avoid the oxidation of the mixture; stir slowly at 200-500 rounds per minute so that small particles float and the larger particles stay at the bottom; (3) At room temperature, add slowly 0.2 ml of 176 mg per ml of vitamin C to the bottom of the calcium carbonate suspension; use the acidity of vitamin C to reduce micron calcium carbonate particles to sub-micron particles; at the end of the reaction when there is no more bubbles, gently heat the reaction mixture to 45° C. and reduce the volume by about 50% under vacuum, and the molar ratio of the vitamin C to calcium carbonate is 1:5; (4) Add the core components, a mixture of vitamin C and calcium carbonate, into the matrix at 5% (w/w), and adjust PH to 7.

Embodiment 3

1. Grind calcium carbonate to a particle size of approximately 2 μm; (2) Suspend calcium carbonate at 100 mg per ml in deionized and nitrogen-saturated water in order to avoid the oxidation of the mixture; stir slowly at 200-500 rounds per minute so that small particles float and the larger particles stay at the bottom; (3) At room temperature, add slowly 0.33 ml of 176 mg per ml of vitamin C to the bottom of the calcium carbonate suspension; use the acidity of vitamin C to reduce micron calcium carbonate particles to sub-micron particles; at the end of the reaction when there is no bubbles, gently heat the reaction mixture to 45° C. and reduce the volume by about 50% under vacuum, and the molar ratio of the vitamin C to calcium carbonate is 1:3; (4) Add the core components, a mixture of vitamin C and calcium carbonate, into the matrix at 10% (w/w), and adjust PH to 7.

Embodiment 4

Figure 9:
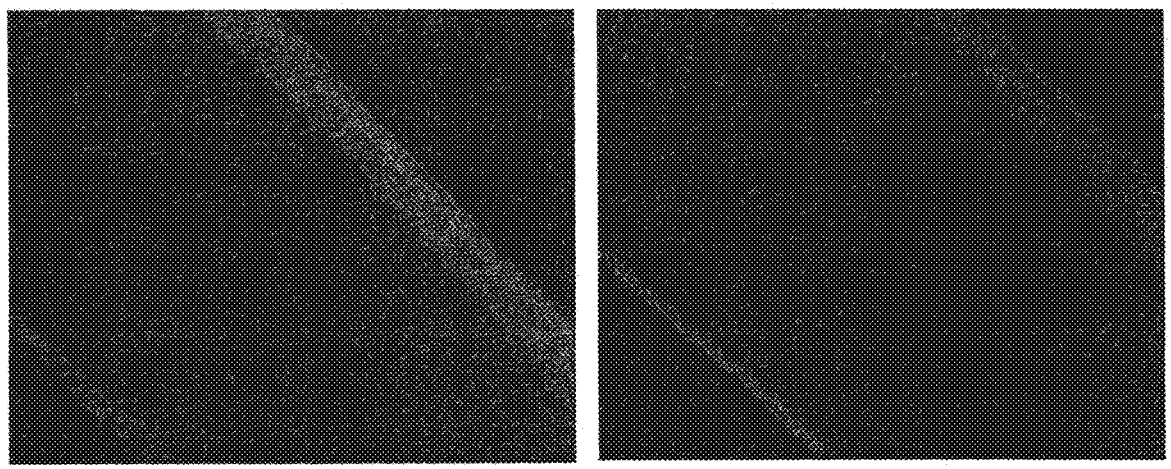
FIG. 9. Comparison of penetrations of submicron and micron particles of calcium carbonate into the three-dimensional skin model.

EFT 400 skin models were obtained from MatTek (Ashland, Mass.). Experiments were divided into two groups. One group is treated with 10 μg/cm² micron particles of calcium carbonate for 24 h; the other group is treated with 10 μg/cm² submicron particles of calcium carbonate for 24 h. After treatment, histological examination was carried out by hematoxylin and eosin staining and calcium levels penetrated into the skin were determined by alizarin staining, respectively. Results show that submicron calcium carbonate particles as prepared by the present invention are more readily that micron particles to enter the skin (FIG. 9).

Embodiment 5

Figure 10:
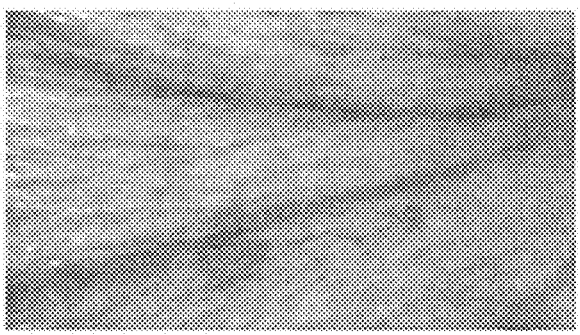
FIG. 10. Skin improvements after using the skincare product of the present invention.
Figure 10:
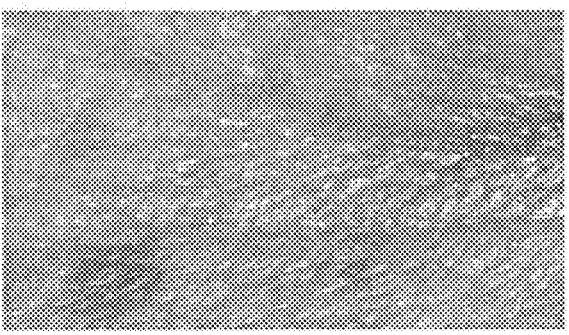
Figure 10:
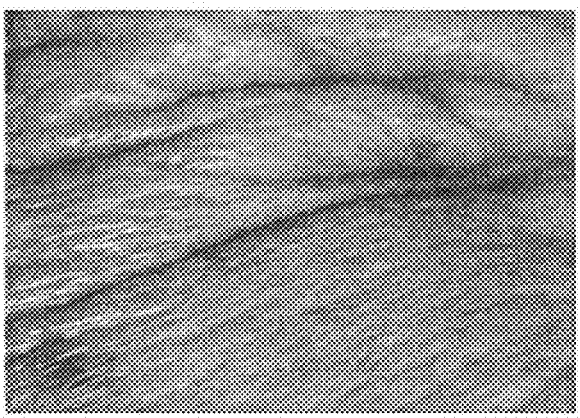
Figure 10:
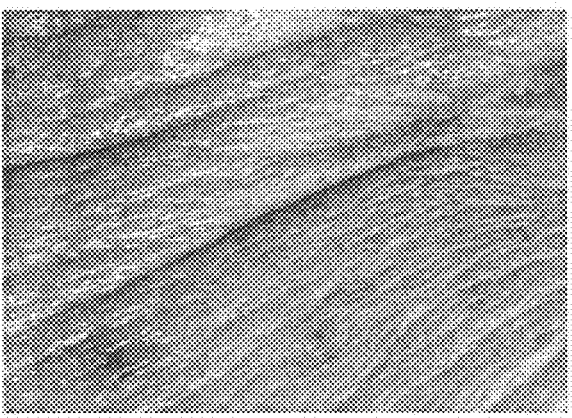

Clinical trial participants were required to take pictures at the corner of the right eye (canthus) before using the product of this invention, and then 3 months after continuous use of the product. Results show that canthus wrinkles after using the product of the invention is significantly reduced, highly improving skin appearance (FIG. 10).

What is claimed is:

1. A skincare product comprising:
    a reducing agent selected from vitamin C, vitamin E, glutathione, vitamin A, vitamin D, and their derivatives; and
    a precipitating agent selected from calcium carbonate, pearl powder, magnesium carbonate, barium carbonate, calcium phosphate, magnesium phosphate, barium phosphate, calcium silicate, calcium molybdate, calcium tungstate, magnesium silicate, magnesium selenite, barium oxalate, barium molybdate, barium manganate, barium selenate, beryllium carbonate, beryllium phosphate, beryllium silicate, strontium carbonate, strontium phosphate, strontium silicate, strontium molybdate, strontium tungstate, strontium selenate, and barium silicate,
    wherein a molar ratio of the reducing agent to the precipitating agent is in a range of 1:3 to 1:6,
    wherein the reducing agent and the precipitating agent together represent 0.1% to 0.5% w/w of the skincare product; and
    wherein a pH of the skincare product is in a range of 5 to 8.

2. The skincare product according to claim 1, wherein the molar ratio of the reducing agent to the precipitating agent is 1:5.

3. The skincare product according to claim 1, wherein the pH of the skin care product is 7.

4. The skincare product according to claim 1, wherein a particle diameter of the precipitating agent is about 0.3 micron to about 1 micron.

5. The skin care product of claim 1, wherein the reducing agent is vitamin C.

6. The skincare product of claim 5, wherein the precipitating agent is calcium carbonate.

7. The skincare product of claim 1, wherein the precipitating agent is calcium carbonate.

8. The skin care product of claim 1, wherein the skin care products is made by:
    a) grinding the precipitating agent to a particle size of 1 to 5 microns;
    b) suspending the particles of the precipitating agent in deionized and nitrogen-saturated water;
    c) adding the reducing agent into the suspension of the precipitating agent,
    wherein the reducing agent is added to precipitating agent such that a molar ratio
    of the reducing agent to the precipitating agent is in the range of 1:3 to 1:6; and
    d) adjusting the pH of the skincare product to about 5 to 8, wherein the reducing agent and the precipitating agent together represent 0.1% to 0.5% (w/w) of the skincare product.

9. The skincare product of claim 8, wherein the precipitating agent is calcium carbonate.

10. The skincare product of claim 8, wherein the reducing agent is vitamin C.

11. The skincare product of claim 10, wherein the precipitating agent is calcium carbonate.

12. A method to prepare the skincare product according to claim 1, comprising the steps of:
    a.) grinding the precipitating agent to a particle size of 1 to 5 microns;
    b) suspending the particles of the precipitating agent in deionized and nitrogen-saturated water;

c) adding the reducing agent into the suspension of the precipitating agent,
wherein the reducing agent is added to precipitating agent such that a molar ratio of the reducing agent to the precipitating agent is in the range of 1:3 to 1:6; and
d) adjusting a pH of the skincare product to about 5 to 8.

13. The method according to claim 12, wherein the particle size in step a) is 1 to 3 micron.

14. The method according to claim 12, further comprising the step of: stirring the precipitating agent in step b) at a speed of 200 to 500 rotations per minute.

15. The method according to claim 12, wherein pH is 7.

\* \* \* \* \*